United States Patent [19]
Kolowich

[11] Patent Number: 6,069,343
[45] Date of Patent: May 30, 2000

[54] PERITONEAL DIALYSIS SOLUTION WARMER

[76] Inventor: J. Bruce Kolowich, 1107 Michigan Ave., Ann Arbor, Mich. 48104

[21] Appl. No.: 09/118,260

[22] Filed: Jul. 17, 1998

Related U.S. Application Data

[60] Provisional application No. 60/052,867, Jul. 17, 1997.

[51] Int. Cl.[7] .................................................. A21B 1/00
[52] U.S. Cl. ........................ 219/399; 219/386; 219/521; 392/470
[58] Field of Search .................................... 219/394, 386, 219/402, 521, 405, 430; 392/470; 604/114

[56] References Cited

U.S. PATENT DOCUMENTS

| | | | |
|---|---|---|---|
| 3,608,627 | 9/1971 | Shevlin | 165/206 |
| 3,764,780 | 10/1973 | Ellis | 219/430 |
| 3,845,273 | 10/1974 | Hurko | 219/462 |
| 3,855,451 | 12/1974 | Lee | 219/400 |
| 3,955,488 | 5/1976 | Wheeler | 99/483 |
| 4,233,495 | 11/1980 | Scoville et al. | 219/386 |
| 4,460,332 | 7/1984 | Lawler et al. | 432/72 |
| 4,495,402 | 1/1985 | Burdick et al. | 219/214 |
| 4,644,136 | 2/1987 | Watchman | 219/400 |
| 4,657,004 | 4/1987 | Coffey | 128/134 |
| 4,707,587 | 11/1987 | Greenblatt | 219/299 |
| 4,734,562 | 3/1988 | Amano et al. | 219/413 |
| 4,849,610 | 7/1989 | Alvarez | 219/521 |
| 4,889,973 | 12/1989 | Farinacci et al. | 219/528 |
| 4,910,386 | 3/1990 | Johnson | 219/385 |
| 4,918,290 | 4/1990 | DeMars | 219/400 |
| 4,927,995 | 5/1990 | Lovett et al. | 219/385 |
| 4,934,336 | 6/1990 | White | 126/263 |
| 4,947,026 | 8/1990 | Groom et al. | 219/401 |
| 5,004,894 | 4/1991 | Whitehead | 219/521 |
| 5,057,671 | 10/1991 | Colson | 219/521 |
| 5,132,518 | 7/1992 | Solacoff | 219/385 |
| 5,183,994 | 2/1993 | Bowles, Sr. et al. | 219/387 |
| 5,282,264 | 1/1994 | Reeves et al. | 392/382 |
| 5,309,981 | 5/1994 | Binder | 165/64 |
| 5,397,875 | 3/1995 | Bechtold, Jr. | 219/521 |
| 5,408,576 | 4/1995 | Bishop | 392/470 |
| 5,442,161 | 8/1995 | Matsushima | 219/756 |
| 5,505,122 | 4/1996 | Gerrit | 219/400 |
| 5,606,640 | 2/1997 | Murphy | 392/382 |
| 5,695,668 | 12/1997 | Boddy | 219/400 |
| 5,786,568 | 7/1998 | McKinney | 219/400 |

*Primary Examiner*—Teresa Walberg
*Assistant Examiner*—Vinod D Patel
*Attorney, Agent, or Firm*—Gifford, Krass, Groh, Sprinkle, Anderson & Citkowski, P.C.

[57] ABSTRACT

A warmer for fluid filled containers includes a cabinet with an interior chamber at face with an opening providing access to the interior chamber. The interior chamber is designed to receive and store multiple fluid filled containers and has an inner surface with a top and a bottom. The exterior surface of the cabinet is separated from the inner surface of the interior chamber by an insulated inner layer. A door is provided for covering the access opening and a rack is provided for supporting fluid filled containers in the interior chamber. A sheathing device, a temperature sensor, and a thermal energy distributor are all located in the interior chamber. The heating device is designed to alter the interior air temperature of the chamber, the sensor is designed to sense the interior temperature, and the energy distributor is designed to distribute thermal energy from the heating device. A temperature control device is in communication with the sensor and the heating device and controls the heating device such that the interior air temperature of the chamber is maintained at a generally constant temperature.

16 Claims, 3 Drawing Sheets

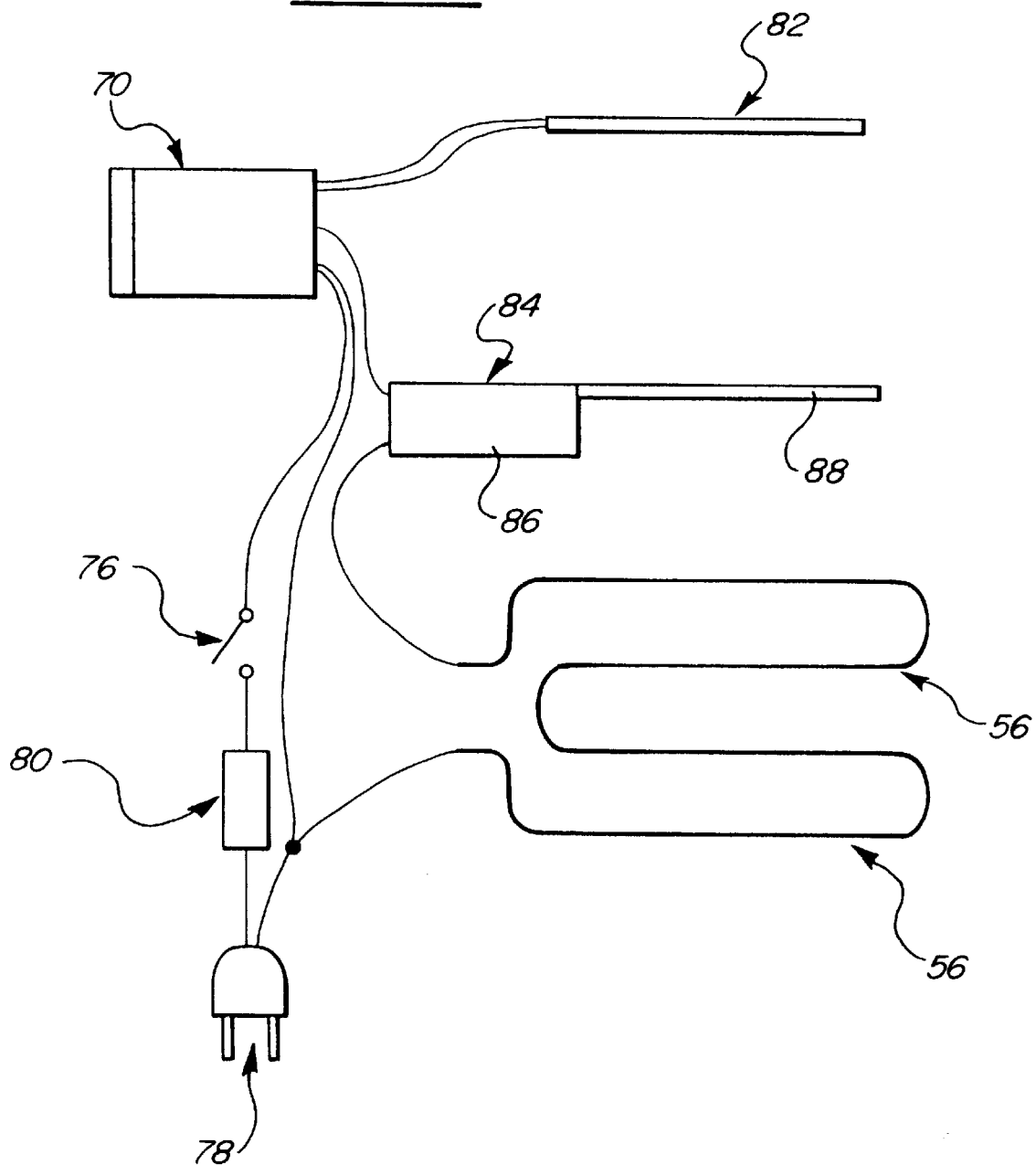

PERITONEAL DIALYSIS SOLUTION WARMER

RELATED APPLICATION

This patent application claims priority from provisional patent application Serial No. 60/052,867 filed Jul. 17, 1997 entitled "Peritoneal Dialysis Solution Warmer."

FIELD OF THE INVENTION

The subject invention relates generally to a warmer for fluid filled containers and more specifically to a warmer for solution bags used in peritoneal dialysis.

BACKGROUND OF THE INVENTION

In a healthy person, the kidneys remove impurities from the blood and eliminate them in the urine. If the kidneys are damaged or cease to function efficiently, impurities can build up leading eventually to death. Dialysis is a medical process used to remove impurities from the body that would otherwise be removed by the kidneys. Hemo dialysis is a process wherein a patient's blood is pumped through a special filtration machine to remove impurities and then pumped back into the body. Because the required equipment is bulky and very expensive, hemo dialysis is usually performed in a dialysis clinic. The patient must visit the clinic for several hours every few days as long as the kidney condition is present. Eventually, many patients receive a kidney transplant preventing any further need for dialysis. However, there are often long waits for transplantable kidneys and consequently the patients must continue dialysis treatments for several years.

As an alternative to hemo dialysis, peritoneal dialysis was developed. The peritoneum is a abdominal membrane located below the diaphragm and separating the stomach, lungs, and heart from the intestines. Below the peritoneum is the peritoneal cavity. In peritoneal dialysis, saline solution is placed in the peritoneal cavity. Because the solution has a higher salinity than other body fluids, fluid is drawn across the peritoneum to dilute the solution. Impurities are also drawn across the peritoneum into the solution. After a period of time, the saline solution is drained from the peritoneal cavity taking the impurities with it. The solution can then be replaced with fresh saline starting the process over.

Peritoneal dialysis has multiple advantages over hemo dialysis. Many doctors and health organizations feel that it is healthier, the necessary equipment is much less expensive, and most patients can perform the process in the privacy of their own home. For peritoneal dialysis, the patient has a catheter surgically implanted into the abdomen. The catheter is used to fill and drain the peritoneal cavity. Once the catheter is installed, the only equipment necessary for peritoneal dialysis is an IV pole to hang the solution bags as the solution is fed into the peritoneal cavity, miscellaneous tubing and valves, and something to warm the solution before use. Reliable patients can be taught to perform all steps required for peritoneal dialysis in the privacy of their own home eliminating the need for frequent clinic visits. While peritoneal dialysis requires fluid changes several times a day, each change can be accomplished in a bedroom instead of a medical clinic. This gives patients increased control over their lives.

Peritoneal dialysis solution generally comes in heavy duty 2 liter bags of various strengths. The patients performs a variety of measurements to determine how well impurities are being eliminated and uses different solution strengths depending on the results. The solutions generally come in three strengths and those with higher salinity pull more impurities out of the body. Typically patients must change fluid 4 or more times a day and they may use two or three different strengths in the same day.

Peritoneal dialysis solution must be warmed to approximately body temperature before it is fed into the peritoneal cavity. Solution that is significantly cooler than body temperature will chill the body, cause cramps and be uncomfortable. Solution that is too hot will also be uncomfortable and may be hazardous. Therefore, there is a need for a device that can consistently warm a dialysis solution bag to a comfortable temperature for use in the peritoneal dialysis solution process.

The peritoneal dialysis solution should not be warmed too quickly or it can lead to nitrogen fixation, popularly known as the bends. The dialysis solution has a certain amount of air dissolved in it. When the solution is warmed, it is less able to hold the air and so the solution becomes super saturated. If the solution were allowed to remain at the warmed temperature for an extended period, some of the air would slowly work its way to the surface until the solution/air mixture reached equilibrium. However, when the solution is rapidly warmed, it is supersaturated with the air. When the freshly warmed solution is fed into the body, it passes through an IV tube and nucleation occurs creating tiny bubbles. These tiny gas bubbles are pulled into the peritoneal cavity along with the solution. These bubbles can then travel throughout the body leading to nitrogen fixation. Patients' sensitivity to this problem varies, but in some patients it creates a painful condition especially in sensitive joints. To prevent the formation of bubbles, the solution must be warmed slowly enough to allow some of the dissolved air to move out of the solution thereby establishing a new equilibrium at the warmed temperature. Therefore, there is a need for a device that can slowly and steadily warm peritoneal dialysis solution so that the formation of tiny bubbles is prevented.

While the peritoneal dialysis process is a significant improvement over hemo dialysis, it remains time consuming and greatly impacts the quality of life of a patient. A patient must test themselves several times a day, choose a proper solution bag, warm the bag slowly to a comfortable temperature being careful not to over or under heat it, drain the old solution out of the cavity, and feed the fresh solution into the cavity. There is a need to make the warming process more convenient. Warming a solution bag four or more times a day consumes a lot of time and its repetitive nature is tiring. The patient must interrupt whatever they are doing at the time for long enough to accomplish all steps of the process. It would be most convenient if solution bags could be kept warm and ready for use, especially if bags of each solution strength could be kept warm. Then, the patient could skip the warming process and proceed immediately to the drain and refill process. Therefore, there is a need for a device that will store a plurality of peritoneal dialysis solution bags at a ready for use temperature.

Since the peritoneal dialysis process is typically performed in the home, any device used for warming the solution must be suited for the home environment. This requires that the device not be overly bulky. Also, most people would rather not make their bedroom look like a doctor's office or a hospital room so a warming device for home use preferably should not look like medical equipment. The use of stainless steel, electronic readouts, and lights should be minimized. Also, a warming device for the home should not be complex, difficult to use, or require daily maintenance or cleaning. Therefore, there is a need for a peritoneal dialysis solution warming device for use in the home that blends in with the home environment, is not overly bulky, is easy to use, and does not require maintenance.

There are a variety of devices which warm solution but all fall short of meeting all of the needs of patients of peritoneal dialysis. Many attempts at fluid warming are aimed at hospital or clinic use and require the removal of the fluid from the container. This introduces a risk of introducing contamination into the fluid and makes the device using this approach unnecessarily complex and difficult to use. Many of these approaches require bulky, complex devices such as a pump to remove the fluid from the container it was stored in. Once the fluid is removed, it is generally exposed to a heating device of some type and then returned to a separate storage container. All parts of the device must be kept sterile if the fluid is to remain uncontaminated. This necessitates laborious cleaning procedures and the use of expensive, easily cleanable materials such as stainless steel. U.S. patents disclosing systems requiring the removal of solution from its container before heating include: U.S. Pat. No. 4,293,762 to Ogawa; U.S. Pat. No. 4,309,592 to Le Boeuf; U.S. Pat. No. 4,464,563 to Jewett; U.S. Pat. No. 4,678,460 to Rosner; U.S. Pat. No. 4,707,587 to Greenblatt; U.S. Pat. No. 4,844,074 to Kurucz; and U.S. Pat. No. 4,906,816 to van Leerdam.

There are also several U.S. patents directed to warming devices that do not require removal of a fluid from its container. However, each device lacks several features of the present invention. U.S. Pat. No. 4,934,336 to White is directed to an apparatus and method for the warming of intravenous equipment consisting of an insulated wrap material having a removable and reusable heat pack. This reference completely lacks the structure of the present invention and fails to provide for a temperature controller that controls the heat output of a heating device in a cabinet such that the temperature in the cabinet is regulated. The heat source in White is a heat pack that is placed in a wrap with the intravenous equipment. The temperature of the solution will vary depending on the energy in the heat pack and temperature will not be maintained for long periods. The White device is also capacity limited and intended only for portable use.

U.S. Pat. No. 4,874,033 to Chatelain et al. and U.S. Pat. No. 4,801,777 to Auerbach are directed to blood product heating methods and apparatuses. Both require the blood products to be submerged in a heated water bath. The present invention is not directed to heating blood products and does not require submersion of the fluid containers in a bath of water. The use of water makes these devices unsuitable for the home since they require access to a water source and drain. The present invention can be used in a bedroom where water is not readily available. The present invention is also significantly more convenient since the fluid filled containers do not have to be dried before use and the warming device does not have to be filled with water.

U.S. Pat. No. 4,657,004 to Coffey discloses a mobile livestock intensive care unit having a temperature controlled fluid/medicine cabinet. This cabinet lacks the specific structure of the present invention, is not suited to use in the home, is not designed to slowly warm solution, is generally vertical rather than generally horizontal, and is not aimed at peritoneal dialysis solution.

U.S. Pat. No. 5,183,994 to Bowles is directed to a heated drug box. The box relies primarily on thermal conduction and lacks the structure of the present invention. It is not designed to slowly warm solution and maintain the temperature. Rather it is directed to preventing the temperature of medicines carried outdoors in cold temperatures from dropping to a temperature that makes working with the medicines impossible or impractical. The box is not directed to peritoneal dialysis solution warming and is not large enough to store a plurality of solution bags. The reference also is not suited for use in the home.

U.S. Pat. No. 5,282,264 is directed to an apparatus for thawing and warming frozen fluids by the circulation of heated air. The reference lacks the structure of the present invention, is bulky, requires a circulation fan, and is designed for thawing frozen fluids rather than maintaining the temperature of ready to use solution.

U.S. Pat. No. 5,408,576 to Bishop is directed to an IV fluid warmer for use in an operating room. A plurality of bags are dropped through a door in the top of the generally vertical cabinet where they contact a heating element mounted on a side wall. Warmed bags are sequentially dispensed from an opening in the side of the unit near its bottom. The reference relies on thermal conduction, provides access only to the bottom-most solution bag, lacks insulation, and is designed to rapidly warm solution rather than to do so slowly. Providing access only to one solution bag at a time prevents the unit from being used to warm a variety of solution strengths. The reference is aimed at operating rooms and therefore is not well suited to home use. It also lacks the specific structure of the present invention.

While solution manufactures recommend against it, many patients warm the solution bags in the microwave. This presents two problems. The temperature of the solution bag is difficult to control. Cooking time will be highly dependent on the starting temperature of the solution bag. It is also difficult for a patient to determine the exact temperature of the bag and consequently they may inadvertently over or under cook the solution. The second problem is that bubble formation is especially prevalent with microwaving because a microwave heats unevenly. The solution will be warmed much faster where the microwave energy is concentrated than where it is not.

SUMMARY OF THE INVENTION

The present invention is directed to a warmer for fluid filled containers. The warmer includes a cabinet with an interior chamber faced with an opening which communicates with the interior chamber. The interior chamber is defined by an inner surface that has a top and a bottom. The cabinet on the exterior surface which is separated from the inner surface of the interior chamber by an insulating inner layer. The interior chamber is designed to receive and store multiple fluid filled containers. The door is provided for covering the access opening in the face of the cabinet. The heating device is located in the interior chamber and is designed to alter the interior air temperature of the chamber. A normal energy distributor is also located in the interior chamber and distributes thermal energy from the heating device. A temperature sensor is located in the interior chamber and in communication with the temperature control device which controls heating devices that the interior air temperature in the interior chamber is maintained at a generally consist temperature.

BRIEF DESCRIPTION OF THE DRAWINGS

FIG. 4 is a schematic for the preferred embodiment of the present invention.

DETAILED DESCRIPTION

Figure 1:
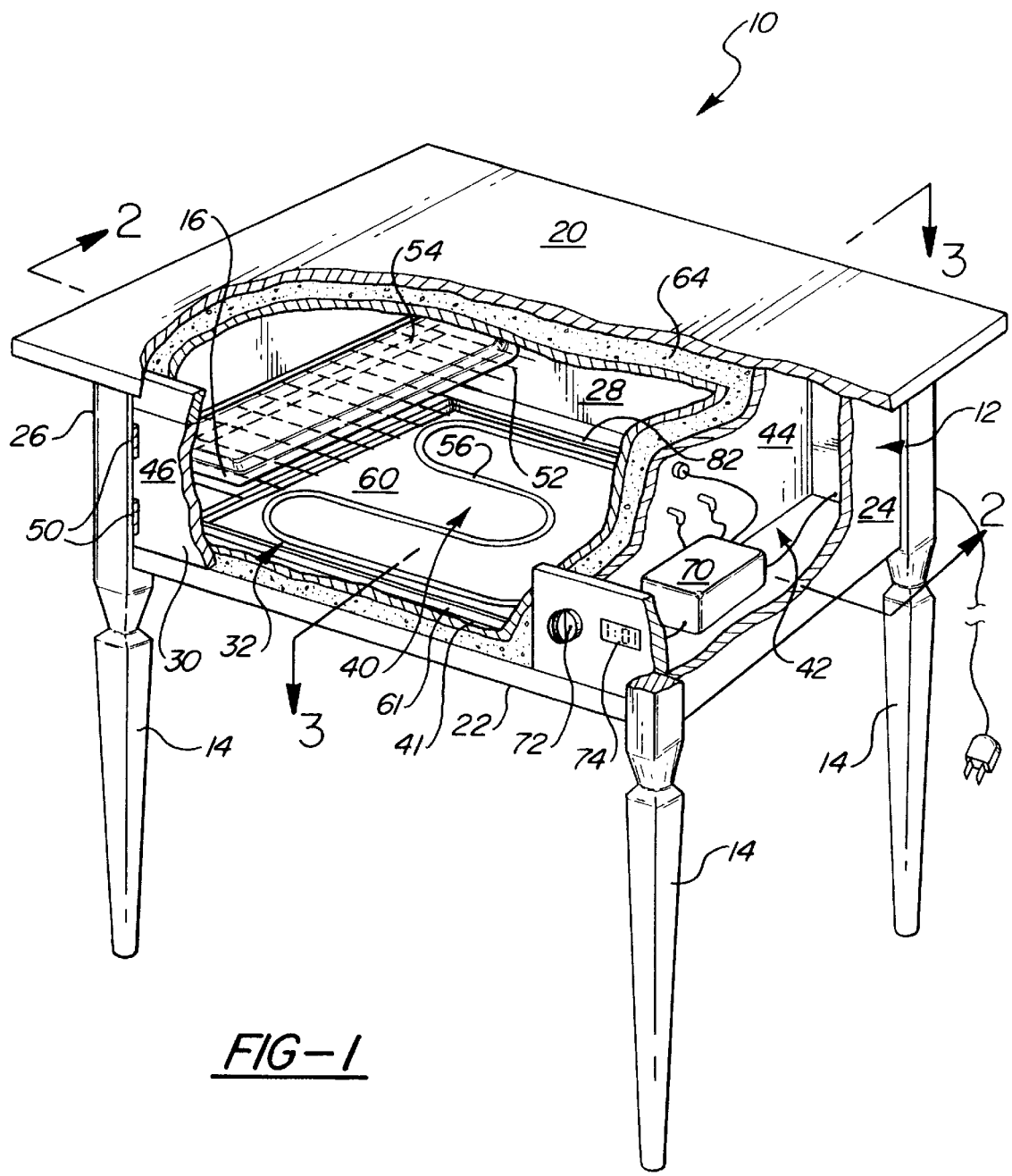
FIG. 1 is a cut-away perspective view of a preferred embodiment of the present invention.
Figure 2:
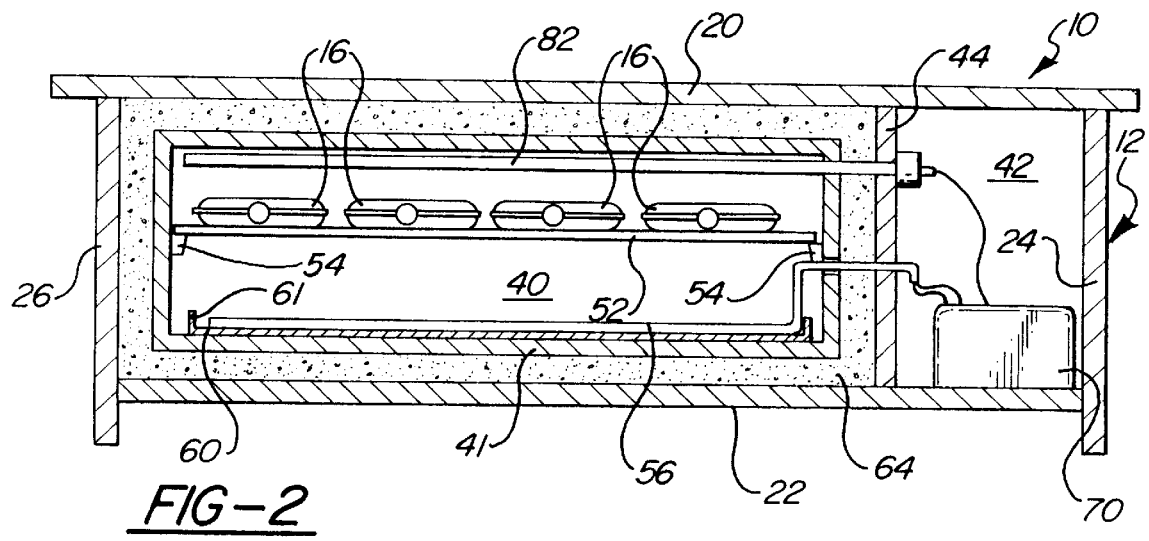
FIG. 2 is a section view taken along lines 2—2 of FIG. 1.
Figure 3:
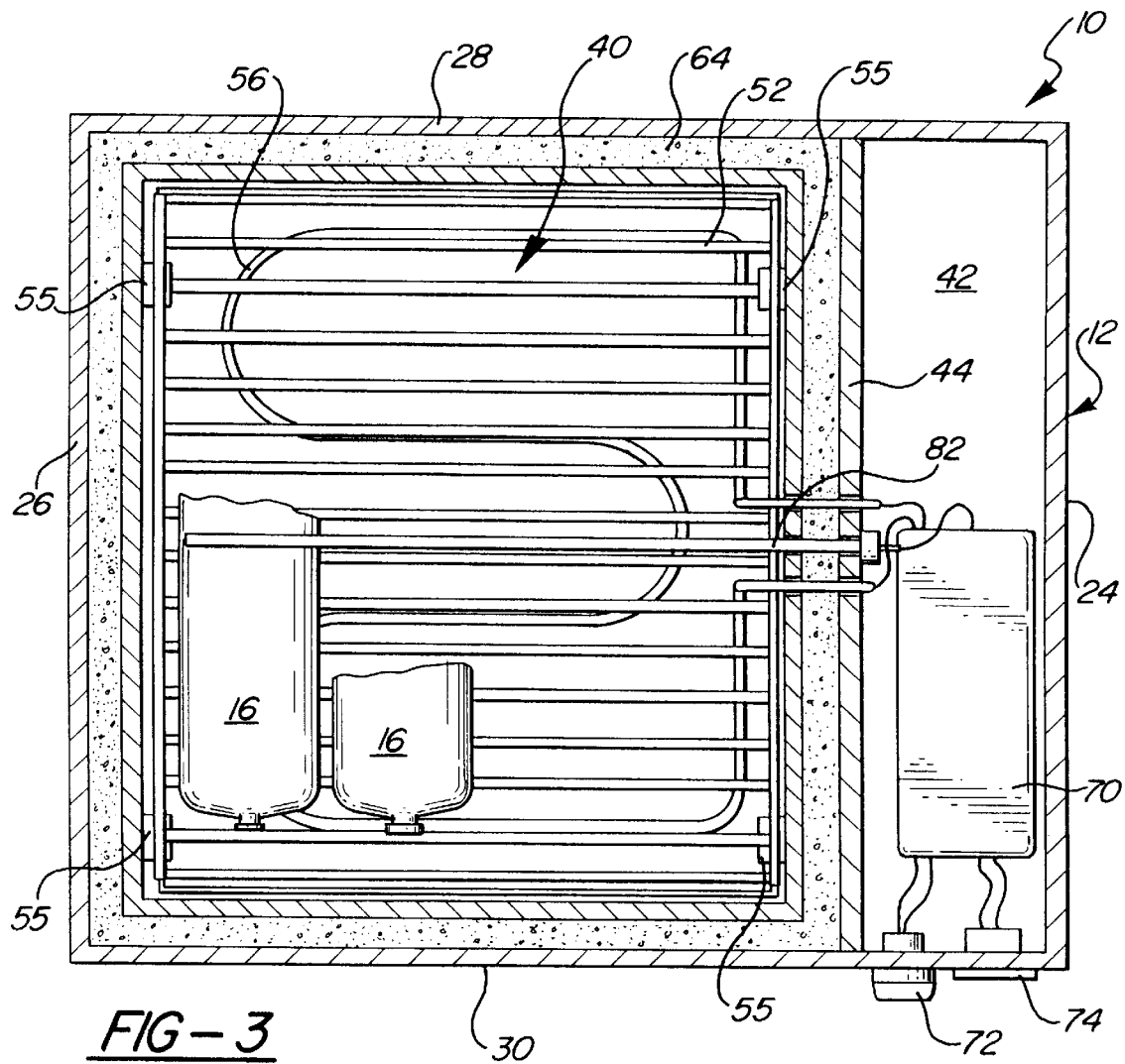
FIG. 3 is a sectional view taken along lines 3—3 of FIG. 1.

Referring to FIGS. 1 through 3, a preferred embodiment of a warmer 10 for fluid filled containers 16 is shown. The warmer 10 comprises a generally horizontal, rectangular parallelepiped (box shaped) cabinet 12 supported by four legs 14. The cabinet 12 has a generally horizontal top 20 and bottom 22 interconnected by two generally vertical sides, 24 and 26, and a generally vertical back 28 and front 30. The cabinet 12 defines an interior area which is divided into a first interior chamber 40 and a second interior chamber 42 by a dividing wall 44. The front 30 of the cabinet 12 includes an access opening 32 defined therein for accessing the first interior chamber 40. A door 46 is supported on the front 30 of the cabinet 12 by hinges 50 so that the door 46 can swing between a first position where the door 46 substantially covers the access opening 32 and a second position where the access opening 32 is uncovered. Alternatively, the door 46 may be located on a different side of the cabinet 12 or may form part or all of the horizontal top 20 so that the top of the cabinet 12 may be opened providing access to the interior chamber 40.

The first interior chamber 40 has a bottom 41 and is configured to store a plurality of fluid filled containers 16 such as one liter saline bags on a horizontal rack 52 (shown with a portion cut away). Preferably, the rack 52 supports four to six saline bags (4 shown). The rack 52 is similar to an oven rack and comprises a plurality of parallel metal bars within a surrounding metal frame. The rack 52 is supported above the bottom 41 of the chamber 40 on two horizontal rails 54 and can be slid on the rails 54 into and out of the access opening 32 when the door 46 is open. Alternatively, the rack 54 can be supported by support blocks 55 as shown in FIG. 3. Preferably, the rack 52 is positioned between 1 and 3 inches above the bottom 41 of the first interior chamber 40 so as to leave an air space below the rack 52. Sliding the rack 52 partially out through the access opening 32 allows improved access to the rack 52 for adding or removing fluid filled containers 16. A stop (not shown) prevents the rack 52 from being accidentally pulled out too far.

A copper sheet 60 is located adjacent and parallel to the bottom 41 of the first interior chamber 40 and covers substantially all of the bottom 41 of the chamber 40. A heating element 56 is disposed in the first interior chamber 40 above the copper sheet 60 and below the rack 52. The heating element 56 illustrated in the figures is similar to the heating elements used in home ovens. This type of heating element works well for this application, but it has been found that the use of flexible electrical resistive heating elements is more preferred. The type of heating element 56 which works particularly well is a silicone rubber resistive heating strip. These strips are water resistant and have low watt densities. Low watt density is desirable as the wooden bottom 41 of the interior chamber 40 should remain below a temperature of 150° Fahrenheit. The use of low watt density heaters reduces the likelihood of hot spots or damage to the wood bottom 41. In one embodiment of the present invention, two 150 Watt silicone rubber electric resistance heat strips are used in series giving a total wattage output of approximately 75 watts.

The copper sheet 60 serves multiple functions. First, the copper sheet 60 prevents heat from the heating element 56 from overheating the bottom 41 of the first chamber 40. As heat is radiated and conducted from the heating element 56, the copper sheet 60 distributes the heat away from the element 56 thereby preventing an over concentration of heat immediately below the element 56. This distribution of heat serves the copper sheet's second function; evenly distributing thermal energy from the heating element 56. It is an important feature of the warmer 10 that fluid filled containers 16 are slowly and evenly warmed. By distributing heat away from the heating element 56, the copper sheet 60 encourages an even distribution of heat in the first interior chamber 40. The third function of the copper sheet is to capture liquid spills. The fluid filled containers 16 typically warmed are very tough and therefore it is unlikely that one would be pierced or ruptured. However, to provide for all contingencies, the edges of the copper sheet 60 are preferably turned up into a peripheral lip 61 so that the sheet 60 forms a pan for capturing liquid. A drain (not shown) is optionally provided in the sheet 60 and bottom 41 for draining spilled liquid out of the first interior chamber 40.

While the use of a copper sheet 60 is preferred, other materials may also be used. A primary criterion is that the material used must have a high thermal conductivity. In its broadest sense, the copper sheet 60 serves as a thermal energy distributor and therefore must have a high thermal conductivity to adequately distribute heat from the heating element 56. Copper has a thermal conductivity of approximately 400 Watts/meter-degree Kelvin. Other materials with high thermal conductivity include pure aluminum with a thermal conductivity of 237 Watts/meter-degree Kelvin when measured at 300 degrees Kelvin, and many aluminum alloys with thermal conductivities above 150 Watts per meter-degree Kelvin. The use of copper is advantageous because of its high thermal conductivity, relatively low cost, and easy workability. It will be clear to one of skill in the art that other materials, as well as other designs of thermal distributors, may be used to serve the same function as the copper sheet. For example, a copper sheet could be positioned above the heating element 56 or heat pipes could be used to distribute the thermal energy. A fan could be used to evenly distribute thermal energy but it is preferred to avoid moving parts.

As shown, the first interior chamber 40 is generally horizontal with a height significantly smaller than its width. This shape is more than an aesthetic choice. By minimizing the height of the first interior chamber 40, the temperature variance within the chamber is reduced. Since heat rises, a generally vertical chamber or a tall chamber would be warmer near its top than near its bottom. Minimizing the height of the chamber 40 helps achieve the goal of maintaining each of the fluid filled containers 16 at the same temperature.

Spacing the rack 52 from the heating element 56 also helps to achieve a design goal of the warmer 10. By spacing the heating element 56 from the rack 52, and the fluid filled containers 16, warming of the containers 16 is accomplished primarily by convection. The heating element 56 warms the air in the first interior chamber 40 and the air, in turn, warms the containers 16. This process is necessarily slow, which in this application is desirable. The containers 16 are slowly warmed to the desired temperature. The use of a low wattage heating element 56 also limits how fast the containers can be warmed.

The first interior chamber 40 is separated from the top 20, bottom 22, side 26, and second interior chamber 42 by a layer of insulation 64 for minimizing the loss of heat from the chamber 40. The door 46 is preferably also insulated.

The insulation is preferably foam but many types of insulation could be used as should be readily apparent to those of skill in the art.

It is also preferred that the exterior of the cabinet 12 and the inner surface of the first interior chamber 40 are wood. The warmer 10 is designed to look like furniture. Since peritoneal dialysis is often performed in the home, the warmer 10 is designed to blend with typical home furnishings. Many patients would rather not be reminded that they are dependent on medical equipment. The design of the warmer 10 avoids the look of medical equipment to help make the room where the warmer 10 is located more comfortable.

Referring now to all of the Figures but especially to FIG. 4, the heating and control system are shown. A primary temperature controller 70 is mounted in the second interior chamber 42. The primary controller 70 adjustably controls the temperature in the first interior chamber 40. The primary controller 70 is preferably an integrated unit with an adjustment knob or buttons and a temperature readout built in. This is the configuration shown in FIG. 4. In FIGS. 1 through 3, an alternative embodiment is shown where a temperature control knob 72 and a temperature readout unit 74 are discrete units and attached to the primary controller 70 by wires. Many versions of temperature controllers are available which can be used in the present invention. However, it is preferred that the temperature control 70 be capable of very precisely controlling the temperature in the first interior chamber 40. It is most preferred that the temperature not be allowed to fluctuate more than 1° Fahrenheit under normal conditions with the door 46 closed and the liquid containers 16 at equilibrium.

Referring now to FIG. 4, a main switch 76 is positioned between the primary controller 70 and a plug 78 designed to be inserted into a wall socket (not shown). The main switch 76 will normally be left in the on position so that power flows to the controller 70 and the fluid filled containers 16 are maintained at an ideal temperature. A fuse block 80 is positioned between the main switch 76 and the plug 80. The fuse block 80 can be any of a variety of available safely switches. It interrupts the flow of power if an electrical overload occurs. A temperature sensor 82 is wired to the primary temperature controller 70 and passes through the dividing wall 44 and into the first interior chamber 40. The temperature sensor 82 is preferably a three wire RTD which is capable of very precisely measuring temperature. The primary temperature controller 70 uses the signal from the thermocouple 82 to determine the temperature in the first interior chamber 40. The heating element 56, which is located adjacent the copper sheet 60 in the first interior chamber 40, is also wired to the primary temperature controller 70. In the embodiments of the present invention using the more preferred flexible electric resistant heating elements, the entire element is disposed within the interior chamber 40 and wires pass from the heating element through the dividing wall 44 to the primary temperature controller 70. The primary temperature controller 70 provides power to the heating element 56 as needed to precisely control the temperature in the first interior chamber 40. A safety controller 84 is wired between the primary temperature controller 70 and the heating element 56. The safety controller 84 includes a body portion 86 which is mounted in the second interior chamber 42 and a temperature sensing portion 88 which passes through the dividing wall 44 and into the first interior chamber 40. The safety controller 84 is a mechanical device which interrupts power to the heating element 56 if the temperature in the first interior chamber 40, as sensed by the temperature sensing portion 88, exceeds a predetermined temperature. The safety controller 84 prevents excessive temperatures in the first interior chamber even if the primary controller 70 fails or is inadvertently set too high.

When a peritoneal dialysis patient first uses the warmer 10, he or she will place a plurality of saline bags 16 of various strengths on the tray 52 and turn the main switch 76 on. The patient will set the temperature control knob 72 for approximately body temperature. Different patients will prefer slightly different temperatures so the patient may need to readjust the knob 72 as they come to know their preferences. The warmer 10 will preferably require a period of 2 or more hours to warm the saline bags 16 to body temperature. The temperature readout unit 74 will display the temperature in the first interior chamber 40. After the saline bags 16 have reached the required temperature, they will stabilize and be maintained at the temperature until needed. When the patient requires a saline bag 16, he or she will choose the desired strength and remove the bag 16 from the warmer 10 through the door 46. The patient may either place another cold saline bag 16 in place of the warmed bag they removed, or may wait and replace several bags at once. The capacity of the warmer 10 allows most patients to refill the warmer 10 just once per day. While the warmer 10 warms the bags 16 slowly to prevent bubble formation, the warming rate is preferably sufficient to warm several bags to body temperature in two to three hours. Since most patients require only 4 bags per day, the period between bags should be greater than the period required to warm a new cold bag. Therefore, the patient is assured that all bags 16 in the warmer 10 are ready for use after a passage of only two to three hours.

I claim:

1. A warmer for fluid filled containers, said warmer comprising:

a cabinet having an interior chamber defined therein and a first face with an access opening defined therein, said access opening communicating with said interior chamber, said interior chamber being defined by an inner surface and having a top and a bottom, said cabinet further having an exterior surface separated from said inner surface by an insulating inner layer, said interior chamber being configured to receive and store a plurality of fluid filled containers and having an interior air temperature associated therewith;

a door pivotally supported by said cabinet and having a first position in which said door substantially covers said access opening and a second position in which said door substantially uncovers said access opening, a rack supported in said interior chamber for supporting the fluid filled containers, said rack spaced from said top and said bottom of said chamber;

a heating device disposed in said interior chamber for altering the interior air temperature thereof;

a thermal energy distributor disposed in said interior chamber for distributing thermal energy from said heating device, said thermal energy distributor comprising a sheet of material having a thermal conductivity greater than 150 Watts/meter-degree Kelvin, said sheet of material disposed adjacent said bottom of said interior chamber and covering substantially all of said bottom of said interior chamber, said sheet further comprising a peripheral lip so that said sheet also defines a catch tray;

a temperature sensor disposed in said interior chamber for sensing the interior air temperature; and a temperature control device in communication with said sensor and said heating device, said control device operative to control said heating device such that the interior air temperature is maintained at a generally constant temperature.

2. The warmer according to claim 1, wherein the thermal conductivity of said sheet of material is greater than 200 Watts/meter-degree Kelvin.

3. The warmer according to claim 1, wherein the thermal conductivity of said sheet of material is greater than 300 Watts/meter-degree Kelvin.

4. The warmer according to claim 1, wherein said sheet of material is a copper sheet.

5. The warmer according to claim 4, wherein said copper sheet is disposed adjacent said heating device.

6. The warmer according to claim 4, wherein said heating device is disposed adjacent said bottom of said interior chamber and said copper sheet is disposed between said heating device and said bottom.

7. The warmer according to claim 1, wherein said heating device comprises an electrical resistance heating element.

8. The warmer according to claim 7, wherein said heating element has a power consumption of less than 150 Watts.

9. The warmer according to claim 7, wherein said heating element has a power consumption of less than 100 Watts.

10. The warmer according to claim 1, wherein said exterior surface of said cabinet is wood.

11. The warmer according to claim 1, wherein said inner surface is wood.

12. The warmer according to claim 1, wherein said door has a wood interior surface and a wood exterior surface separated by an insulating inner layer.

13. The warmer according to claim 1, wherein said interior chamber has a width and a height associated therewith, said width being at least 2 times said height.

14. The warmer according to claim 1, wherein said temperature control device is adjustable.

15. The warmer according to claim 1, further comprising a secondary temperature controller connected between said temperature control device and said heating device and operative to interrupt the communication between said temperature control device and said heating device when said interior air temperature exceeds a predetermined temperature thereby preventing said interior temperature from reaching a predetermined dangerous temperature level.

16. A warmer for fluid filled containers, said warmer comprising:

a cabinet having an interior chamber defined therein and a first face with an access opening defined therein, said access opening communicating with said interior chamber, said interior chamber being defined by a wood interior surface and having a top and a bottom, said cabinet further having a wood exterior surface separated from said interior surface by an insulating inner layer, said interior chamber being configured to receive and store a plurality of fluid filled containers, said chamber having an interior air temperature associated therewith;

a door pivotally supported by said cabinet and having a first position in which said door substantially covers said access opening and a second position in which said door is positioned away from said access opening, said door having a wood interior surface and a wood exterior surface separated by an insulating inner layer;

a rack supported within said interior chamber for supporting the fluid filled containers, said rack spaced from said top and said bottom of said chamber;

an electrical resistance heating element disposed adjacent said bottom of said interior chamber for altering the interior air temperature;

a thermal energy distributor disposed in said interior chamber for distributing thermal energy from said heating device, said thermal energy distributor comprising a sheet disposed adjacent and parallel to said bottom of said interior chamber between said bottom and said heating device;

a temperature sensor disposed in said chamber for sensing the interior air temperature; and an adjustable temperature control device in communication with said sensor and said heating device and operative to control said heating device such that the interior air temperature is maintained at a generally constant temperature.

* * * * *

UNITED STATES PATENT AND TRADEMARK OFFICE
CERTIFICATE OF CORRECTION

PATENT NO. : 6,069,343
DATED : May 30, 2000
INVENTOR(S) : J. Bruce Kolowich

It is certified that error appears in the above-identified patent and that said Letters Patent is hereby corrected as shown below:

Abstract, line 2 - Delete "at" and insert --and a--

Abstract, line 10 - Delete "sheathing" and insert --heathing--

Column 4, line 47 - After "chamber" insert a --.--

Column 4, line 47 - Delete "face with an opening" and insert --An opening in one face of the cabinet--

Column 4, line 47 - Delete --which--

Column 4, line 50 - Replace "on the" with --has an--

Column 4, line 53 - Replace "The" with --A--

Column 4, line 54 - Replace "The" with --A--

Column 4, line 57 - Replace "normal" with --thermal--

Column 4, line 61 - After "controls" insert --the--

Column 4, line 61 - Replace "devices" with --device so--

Column 4, line 63 - Replace "consist" with --consistent--

Column 7, line 40 - Replace "safely" with --safety--

Signed and Sealed this

Fifteenth Day of May, 2001

Attest:

NICHOLAS P. GODICI

Attesting Officer

Acting Director of the United States Patent and Trademark Office